(12) United States Patent
Cowe

(10) Patent No.: US 10,806,865 B2
(45) Date of Patent: *Oct. 20, 2020

(54) INJECTOR APPARATUS HAVING A CLUTCH TO INHIBIT FORWARD MOVEMENT OF THE PLUNGER

(71) Applicant: OWEN MUMFORD LIMITED, Oxford (GB)

(72) Inventor: Toby Cowe, Oxford (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,001

(22) Filed: Jul. 8, 2016

(65) Prior Publication Data

US 2016/0317752 A1  Nov. 3, 2016

Related U.S. Application Data

(60) Division of application No. 13/639,167, filed as application No. PCT/GB2010/051740 on Oct. 15, (Continued)

(30) Foreign Application Priority Data

Oct. 16, 2009 (GB) .................................... 0918145.4
Mar. 17, 2010 (GB) .................................... 1004440.2

(51) Int. Cl.
*A61M 5/20* (2006.01)
*A61M 5/315* (2006.01)
(Continued)

(52) U.S. Cl.
CPC .......... *A61M 5/31553* (2013.01); *A61M 5/20* (2013.01); *A61M 5/2033* (2013.01); (Continued)

(58) Field of Classification Search
CPC .......... A61M 5/31536; A61M 5/31571; A61M 5/31548; A61M 5/31553; A61M 5/31556;
(Continued)

(56) References Cited

U.S. PATENT DOCUMENTS 5,092,842 A   3/1992  Bechtold et al.
5,104,380 A   4/1992  Holman et al.
(Continued)

FOREIGN PATENT DOCUMENTS

DE   20112501   12/2002
DE   10163325   2/2003
(Continued)

OTHER PUBLICATIONS

Search Report, dated Feb. 9, 2010, in Application No. GB0918145.4.
(Continued)

*Primary Examiner* — Jenna Zhang
(74) *Attorney, Agent, or Firm* — Nixon & Vanderhye

(57) ABSTRACT

An injector apparatus includes a housing ($10^1$, $10^2$) for a cartridge or syringe, a plunger (40) for cooperating in use with the cartridge or syringe to express successive doses, a dose setting arrangement (16, 20) to select a dose volume, and a drive mechanism (22, 24) releasable to advance the plunger in respective predetermined increments of magnitude to express the successive doses. The drive mechanism includes a drive spring (22) for imparting movement directly or indirectly to the plunger (40), and the dose setting arrangement includes a dose setting element (16) moveable in a dose setting routine to define a magnitude of an increment of movement of the plunger for a given dose. The drive mechanism further includes a clutch arrangement (56) operable during the dose setting routine to inhibit forward (Continued)

movement of the plunger and/or to isolate the dose setting element from the force of the drive spring.

15 Claims, 5 Drawing Sheets

Related U.S. Application Data 2010, now Pat. No. 9,415,165, which is a continuation of application No. 12/604,782, filed on Oct. 23, 2009, now Pat. No. 8,608,708.

(60) Provisional application No. 61/314,876, filed on Mar. 17, 2010.

(51) Int. Cl.
*A61M 5/30* (2006.01)
*A61M 5/24* (2006.01)
*A61M 5/31* (2006.01)

(52) U.S. Cl.
CPC .......... *A61M 5/24* (2013.01); *A61M 5/31536* (2013.01); *A61M 5/31551* (2013.01); *A61M 5/315* (2013.01); *A61M 5/3129* (2013.01); *A61M 5/31548* (2013.01); *A61M 5/31556* (2013.01); *A61M 5/31558* (2013.01); *A61M 5/31561* (2013.01); *A61M 5/31575* (2013.01); *A61M 5/31583* (2013.01); *A61M 5/31585* (2013.01); *A61M 2005/2407* (2013.01); *A61M 2005/2492* (2013.01); *A61M 2005/3103* (2013.01); *A61M 2205/581* (2013.01); *A61M 2205/583* (2013.01)

(58) Field of Classification Search
CPC .......... A61M 5/31558; A61M 5/31561; A61M 5/31575; A61M 5/31585; A61M 5/31565; A61M 5/31533; A61M 2005/3125; A61M 2005/3126
See application file for complete search history.

(56) References Cited

U.S. PATENT DOCUMENTS

| | | |
|---|---|---|
| 5,226,896 A | 7/1993 | Harris |
| 5,304,152 A | 4/1994 | Sams |
| 5,320,609 A * | 6/1994 | Haber ............... A61M 5/2033 604/135 |
| 5,300,041 A | 8/1994 | Haber et al. |
| 5,383,865 A | 1/1995 | Michel |
| 5,480,387 A | 1/1996 | Gabriel et al. |
| 5,514,097 A | 5/1996 | Knauer |
| 5,545,147 A | 8/1996 | Harris |
| 5,584,815 A | 12/1996 | Pawelka et al. |
| 5,626,566 A | 5/1997 | Petersen et al. |
| 5,674,204 A | 10/1997 | Chanoch |
| 5,891,086 A | 4/1999 | Weston |
| 5,921,966 A | 7/1999 | Bendek et al. |
| 5,938,642 A | 8/1999 | Burroughs et al. |
| 5,957,896 A | 9/1999 | Bendek et al. |
| 6,193,698 B1 | 2/2001 | Kirchhofer et al. |
| 6,221,053 B1 | 4/2001 | Walters et al. |
| 6,248,095 B1 | 6/2001 | Giambattista et al. |
| 6,290,679 B1 | 9/2001 | Hostettler et al. |
| 6,364,860 B1 | 4/2002 | Steck et al. |
| 6,524,280 B2 | 2/2003 | Hansen et al. |
| 6,582,404 B1 | 6/2003 | Klitgaard et al. |
| 6,699,224 B2 | 3/2004 | Kirchhofer et al. |
| 6,899,698 B2 | 5/2005 | Sams |
| 6,899,699 B2 | 5/2005 | Enggaard |
| 6,932,794 B2 | 8/2005 | Giambattista et al. |
| 6,936,032 B1 | 8/2005 | Bush, Jr. et al. |
| 6,972,007 B2 | 12/2005 | Geiser et al. |
| 7,090,662 B2 | 8/2006 | Wimpenny et al. |
| 7,169,132 B2 | 1/2007 | Bendek et al. |
| 7,195,616 B2 | 3/2007 | Diller et al. |
| 7,241,278 B2 | 7/2007 | Moller |
| 7,297,136 B2 | 11/2007 | Wyrick |
| 7,361,161 B2 | 4/2008 | Bainton |
| 7,553,299 B2 | 6/2009 | Veasey et al. |
| 7,628,773 B2 | 12/2009 | Graf et al. |
| 7,704,238 B2 | 4/2010 | Diller et al. |
| 7,731,698 B2 | 6/2010 | Geiser et al. |
| 7,771,398 B2 | 8/2010 | Knight et al. |
| 7,850,662 B2 | 12/2010 | Veasey et al. |
| 7,896,850 B2 | 3/2011 | Kronestedt et al. |
| 7,905,867 B2 | 3/2011 | Veasey et al. |
| 7,935,088 B2 | 5/2011 | Veasey et al. |
| 7,955,303 B2 | 6/2011 | Burren et al. |
| 7,918,833 B2 | 8/2011 | Veasey et al. |
| 7,993,301 B2 | 8/2011 | Boyd et al. |
| 8,491,538 B2 | 7/2013 | Kohlbrenner et al. |
| 2001/0014791 A1 | 8/2001 | Hansen et al. |
| 2001/0039394 A1 | 11/2001 | Weston |
| 2002/0007154 A1 | 1/2002 | Hansen et al. |
| 2002/0016571 A1 | 2/2002 | Kirchhofer et al. |
| 2002/0120235 A1 | 8/2002 | Enggaard |
| 2003/0160072 A1 | 8/2003 | Geiser et al. |
| 2003/0176841 A1 | 9/2003 | Bainton |
| 2004/0030299 A9 | 2/2004 | Kirchhofer et al. |
| 2004/0054326 A1* | 3/2004 | Hommann ........ A61M 5/31583 604/131 |
| 2004/0059299 A1 | 3/2004 | Moller |
| 2004/0127858 A1 | 7/2004 | Bendek et al. |
| 2004/0186441 A1 | 9/2004 | Graf et al. |
| 2004/0186442 A1 | 9/2004 | Graf et al. |
| 2004/0199117 A1 | 10/2004 | Giambattista |
| 2004/0210199 A1* | 10/2004 | Atterbury ......... A61M 5/31535 604/224 |
| 2004/0215152 A1 | 10/2004 | Kirchhofer et al. |
| 2004/0249348 A1 | 12/2004 | Wimpenny et al. |
| 2004/0267207 A1 | 12/2004 | Veasey et al. |
| 2004/0267208 A1 | 12/2004 | Veasey et al. |
| 2005/0033244 A1 | 2/2005 | Veasey et al. |
| 2005/0055011 A1 | 3/2005 | Enggaard |
| 2005/0113765 A1 | 5/2005 | Veasey et al. |
| 2005/0187523 A1 | 8/2005 | Giambattista |
| 2005/0209570 A1 | 9/2005 | Moller |
| 2005/0251103 A1 | 11/2005 | Steffen et al. |
| 2005/0261634 A1* | 11/2005 | Karlsson ............ A61M 5/2033 604/197 |
| 2006/0069355 A1 | 3/2006 | Judson et al. |
| 2006/0116647 A1 | 6/2006 | Geiser et al. |
| 2006/0184117 A1 | 8/2006 | Knight et al. |
| 2006/0247581 A1 | 11/2006 | Pedersen et al. |
| 2006/0254788 A1 | 11/2006 | Bucher |
| 2006/0258988 A1* | 11/2006 | Keitel ............... A61M 5/31551 604/181 |
| 2006/0264839 A1 | 11/2006 | Veasey et al. |
| 2006/0276754 A1 | 12/2006 | Kronestedt et al. |
| 2006/0287630 A1 | 12/2006 | Hommann |
| 2007/0093761 A1 | 4/2007 | Veasey et al. |
| 2007/0123829 A1 | 5/2007 | Atterbury et al. |
| 2007/0129687 A1* | 6/2007 | Marshall ............ A61M 5/3155 604/207 |
| 2007/0167921 A1 | 7/2007 | Burren et al. |
| 2007/0225657 A1 | 9/2007 | Hommann |
| 2007/0233015 A1 | 10/2007 | Saki |
| 2007/0244436 A1 | 10/2007 | Saiki |
| 2007/0270761 A1 | 11/2007 | Kirchhofer et al. |
| 2007/0270762 A1 | 11/2007 | Kirchhofer et al. |
| 2007/0276341 A1 | 11/2007 | Graf et al. |
| 2008/0015511 A1 | 1/2008 | Veasey et al. |
| 2008/0051713 A1 | 2/2008 | Kohlbrenner et al. |
| 2008/0065026 A1 | 3/2008 | Moller |
| 2008/0077095 A1 | 3/2008 | Kirchhofer |
| 2008/0108953 A1 | 5/2008 | Moser et al. |
| 2008/0114305 A1 | 5/2008 | Gerondale |
| 2008/0119796 A1 | 5/2008 | Graf et al. |
| 2008/0154211 A1 | 6/2008 | Moller |
| 2008/0018313 A1 | 7/2008 | Burren et al. |
| 2008/0183139 A1 | 7/2008 | Burren et al. |

(56) References Cited

U.S. PATENT DOCUMENTS

| | | | |
|---|---|---|---|
| 2008/0188797 A1 | 8/2008 | Enggaard | |
| 2008/0208144 A1 | 8/2008 | Moller | |
| 2008/0234634 A1 | 9/2008 | Eiland et al. | |
| 2008/0243087 A1 | 10/2008 | Enggaard et al. | |
| 2008/0269688 A1 | 10/2008 | Colucci et al. | |
| 2008/0281275 A1 | 11/2008 | Moller | |
| 2008/0287883 A1 | 11/2008 | Radmer et al. | |
| 2008/0306445 A1* | 12/2008 | Burren | A61M 5/24 604/136 |
| 2008/0312605 A1* | 12/2008 | Saiki | A61M 5/31511 604/211 |
| 2009/0054846 A1 | 2/2009 | Moser et al. | |
| 2009/0054850 A1 | 2/2009 | Moser et al. | |
| 2009/0054851 A1 | 2/2009 | Radmer et al. | |
| 2009/0095777 A1 | 4/2009 | Francavilla | |
| 2009/0137964 A1 | 5/2009 | Enggaard et al. | |
| 2009/0198193 A1 | 8/2009 | Veasey et al. | |
| 2009/0209920 A1 | 8/2009 | Moller et al. | |
| 2009/0240195 A1 | 9/2009 | Schrul et al. | |
| 2009/0247951 A1 | 10/2009 | Kohlbrenner et al. | |
| 2009/0247959 A1 | 10/2009 | Kohlbrenner et al. | |
| 2009/0247960 A1 | 10/2009 | Kohlbrenner | |
| 2009/0254035 A1 | 10/2009 | Kohlbrenner et al. | |
| 2009/0254044 A1 | 10/2009 | Kohlbrenner et al. | |
| 2009/0254045 A1 | 10/2009 | Jost | |
| 2009/0254047 A1 | 10/2009 | Thogersen et al. | |
| 2009/0264828 A1 | 10/2009 | Dette et al. | |
| 2009/0275914 A1 | 11/2009 | Harms et al. | |
| 2009/0275915 A1 | 11/2009 | Harms et al. | |
| 2009/0287162 A1 | 11/2009 | Veasey et al. | |
| 2009/0293870 A1 | 12/2009 | Brunnberg et al. | |
| 2009/0299278 A1 | 12/2009 | Lesch et al. | |
| 2009/0299297 A1 | 12/2009 | Moller et al. | |
| 2009/0308386 A1 | 12/2009 | Kronestedt et al. | |
| 2010/0036320 A1 | 2/2010 | Cox et al. | |
| 2010/0069845 A1 | 3/2010 | Marshall et al. | |
| 2010/0094205 A1 | 4/2010 | Boyd et al. | |
| 2010/0094206 A1 | 4/2010 | Boyd et al. | |
| 2010/0094207 A1 | 4/2010 | Boyd et al. | |
| 2010/0094253 A1 | 4/2010 | Boyd et al. | |
| 2010/0106098 A1 | 4/2010 | Atterbury et al. | |
| 2010/0114025 A1 | 5/2010 | Moller | |
| 2010/0114037 A1 | 5/2010 | Moser et al. | |
| 2010/0145305 A1 | 6/2010 | Alon | |
| 2010/0152667 A1 | 6/2010 | Kietzmann | |
| 2010/0152671 A1 | 6/2010 | Raab et al. | |
| 2010/0168677 A1 | 7/2010 | Gabriel et al. | |
| 2010/0179485 A1 | 7/2010 | Radmer et al. | |
| 2010/0186739 A1* | 7/2010 | Kronestedt | A61M 15/0045 128/203.12 |
| 2010/0238038 A1 | 9/2010 | Kohlbrenner et al. | |
| 2010/0241066 A1 | 9/2010 | Hansen et al. | |
| 2010/0312196 A1 | 12/2010 | Hirschel et al. | |
| 2010/0318060 A1 | 12/2010 | Miller et al. | |
| 2010/0324493 A1 | 12/2010 | Plumptre | |
| 2010/0324495 A1 | 12/2010 | Jones | |
| 2010/0324499 A1 | 12/2010 | Nielsen | |
| 2010/0324527 A1 | 12/2010 | Plumptre | |
| 2010/0331788 A1 | 12/2010 | Plumptre et al. | |
| 2010/0331792 A1 | 12/2010 | Plumptre et al. | |
| 2011/0028911 A1 | 2/2011 | Veasey et al. | |
| 2011/0034902 A1 | 2/2011 | Markussen | |
| 2011/0098658 A1 | 4/2011 | Enggaard et al. | |
| 2011/0106008 A1 | 5/2011 | Kronestedt | |
| 2011/0130723 A1 | 6/2011 | Hirschel et al. | |
| 2011/0152784 A1 | 6/2011 | Veasey et al. | |
| 2012/0197213 A1 | 8/2012 | Kohlbrenner et al. | |

FOREIGN PATENT DOCUMENTS

| | | |
|---|---|---|
| DE | 10163326 | 2/2003 |
| DE | 10163327 | 2/2003 |
| DE | 10163328 | 2/2003 |
| DE | 10163329 | 2/2003 |
| DE | 102004063650 | 7/2006 |
| DE | 102005008280 | 7/2006 |
| DE | 102005023823 | 11/2006 |
| DE | 102005023854 | 11/2006 |
| EP | 2101850 | 2/1987 |
| EP | 0338806 | 10/1989 |
| EP | 0615762 | 9/1994 |
| EP | 1304129 | 4/2003 |
| EP | 1542744 | 6/2005 |
| EP | 1601397 | 7/2005 |
| EP | 1683537 | 7/2006 |
| EP | 1683538 | 7/2006 |
| EP | 2125081 | 12/2009 |
| EP | 2196232 | 6/2010 |
| EP | 2196233 | 6/2010 |
| EP | 2210634 | 7/2010 |
| EP | 2258425 | 12/2010 |
| EP | 2263724 | 12/2010 |
| EP | 2283886 | 2/2011 |
| HK | 1070848 | 8/2009 |
| JP | H0271758 | 3/1990 |
| JP | H11514242 | 12/1999 |
| JP | 2008-526279 | 7/2008 |
| JP | 2008-541932 | 11/2008 |
| JP | 2009517157 | 4/2009 |
| JP | 2011519599 | 7/2011 |
| JP | 2011519601 | 7/2011 |
| WO | 9426331 | 11/1994 |
| WO | 9632973 | 10/1996 |
| WO | 09938554 | 8/1999 |
| WO | 200023133 | 4/2000 |
| WO | 200041754 | 7/2000 |
| WO | 200119434 | 3/2001 |
| WO | 200141838 | 6/2001 |
| WO | 02/092153 | 10/2003 |
| WO | 200464902 | 8/2004 |
| WO | 2004078240 | 9/2004 |
| WO | 2006037434 | 4/2006 |
| WO | 2006039930 | 4/2006 |
| WO | 200679898 | 8/2006 |
| WO | 200679900 | 8/2006 |
| WO | 2006126902 | 11/2006 |
| WO | 2006/130100 | 12/2006 |
| WO | 200717051 | 2/2007 |
| WO | 2007063342 | 6/2007 |
| WO | 2008020023 A1 | 2/2008 |
| WO | 2008031236 | 3/2008 |
| WO | 2008059385 | 5/2008 |
| WO | 2008116766 | 10/2008 |
| WO | 2008155144 | 12/2008 |
| WO | 2009/098502 | 8/2009 |
| WO | 200997934 | 8/2009 |
| WO | 2009098299 | 8/2009 |
| WO | 2009126596 | 10/2009 |
| WO | 2009132778 | 11/2009 |
| WO | 2009150028 | 12/2009 |
| WO | 201033790 | 3/2010 |
| WO | 201033795 | 3/2010 |
| WO | 201066796 | 6/2010 |
| WO | 201066797 | 6/2010 |
| WO | 201072662 | 7/2010 |
| WO | 201084164 | 7/2010 |
| WO | 201089418 | 8/2010 |
| WO | 201097125 | 9/2010 |
| WO | 2010112558 | 10/2010 |
| WO | 2010139629 | 12/2010 |
| WO | 2010139630 | 12/2010 |
| WO | 2010139632 | 12/2010 |
| WO | 2010139643 | 12/2010 |
| WO | 2010149717 | 12/2010 |
| WO | 201103762 | 1/2011 |
| WO | 201125448 | 3/2011 |
| WO | 201126928 | 3/2011 |
| WO | 201139233 | 4/2011 |
| WO | 201139239 | 4/2011 |

(56) References Cited

FOREIGN PATENT DOCUMENTS

| WO | 201167320 | 6/2011 |
|---|---|---|
| WO | 201181867 | 7/2011 |

OTHER PUBLICATIONS

Search Report, dated Mar. 30, 2010, in Application No. GB0918145.4.
Search Report, dated Jun. 29, 2010, in Application No. GB1004440.2.
GB search report dated Feb. 8, 2010 in corresponding GB0918145.4.
GB search report dated Mar. 26, 2010 in corresponding GB0918145.4.
GB search report dated Jun. 29, 2010 in corresponding GB1004440.2.
International search report dated May 31, 2011 in corresponding PCT/GB2010/051740.
Translation of Japanese Office Action, dated May 13, 2014, from corresponding JP application.
May 26, 2017, EP communication issued for related EP application No. 13152463.9.
First Examination Report dated Feb. 21, 2019 in the corresponding Indian Patent Application No. 3078/DELNP/2012.
Japanese Office Action for Application No. 2018-054673, dated Mar. 5, 2019, with English translation provided.

* cited by examiner

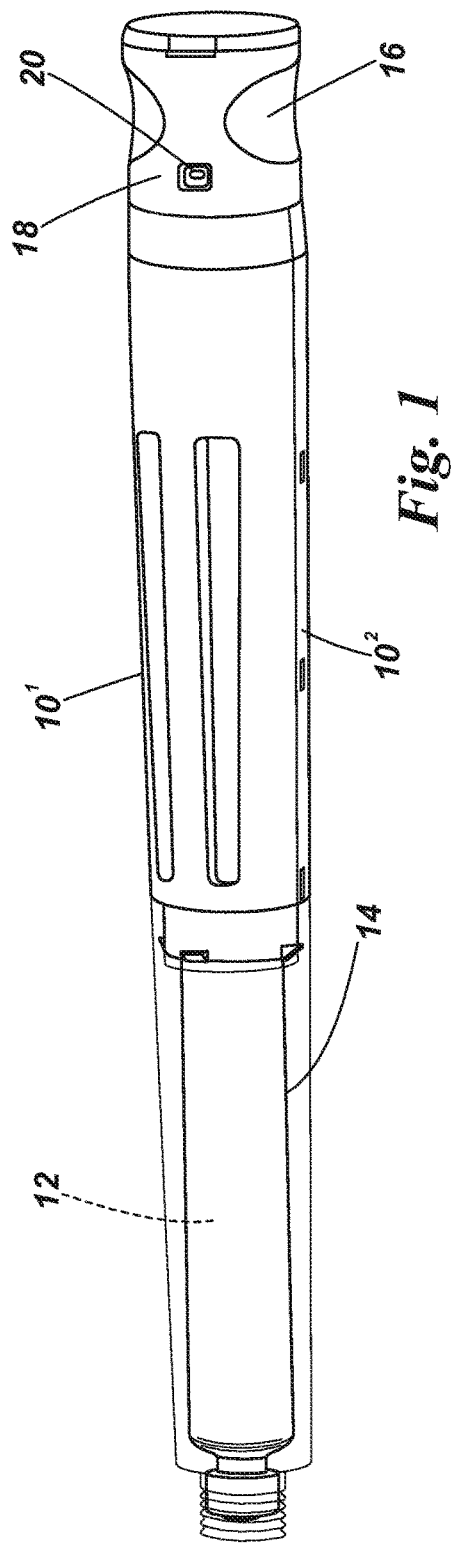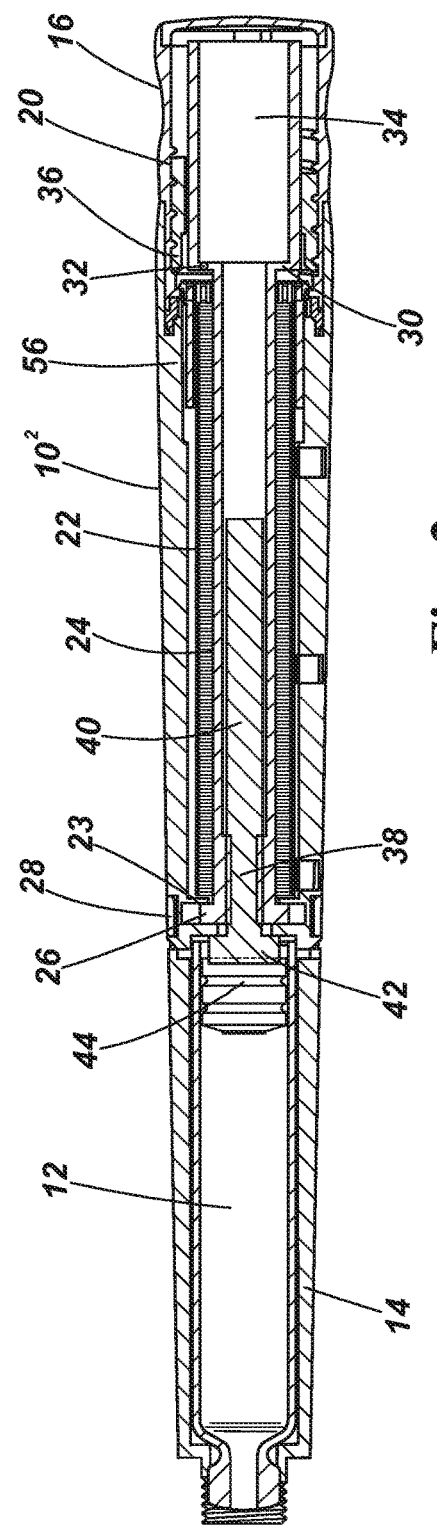

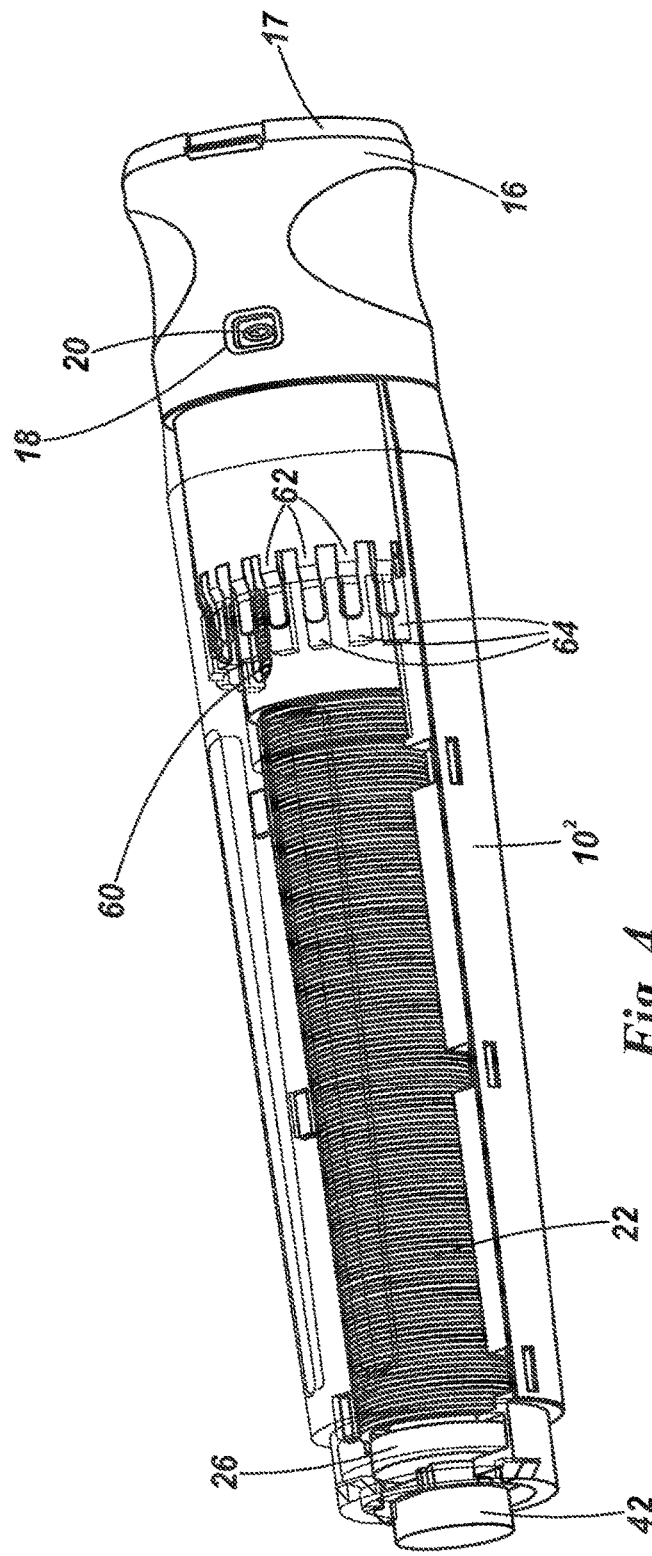
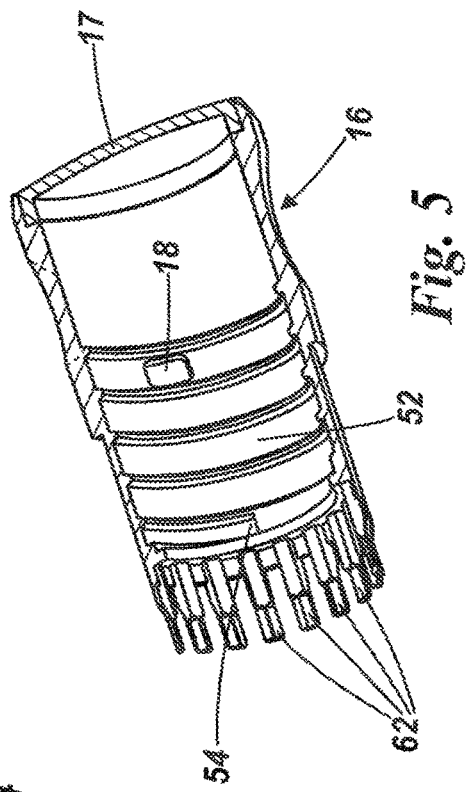

INJECTOR APPARATUS HAVING A CLUTCH TO INHIBIT FORWARD MOVEMENT OF THE PLUNGER

This invention relates to injector apparatus and in particular, but not exclusively, to such apparatus used for injecting multiple doses of variable magnitude, for example of insulin.

BACKGROUND OF THE INVENTION

In our earlier Autopen® device, a rotatable dose setting knob attached to the rear end of the pen injector is connected to a hollow drive sleeve that carries an annular ratchet surface at its front end which engages a corresponding ratchet surface on a threaded drive collar. The threaded drive collar is threadedly engaged with the stem of a plunger so that rotary movement of the drive collar is converted into a linear advance of the plunger. A trigger can be moved to release the drive collar for rotary movement. During a dose setting routine, with the drive collar held against rotation by the trigger, a dose is dialled in by rotating the dose setting knob and the drive sleeve against a spring bias provided by a main drive spring. The dose setting movement is unidirectional only due to the ratchet action between the drive sleeve and the drive collar. Upon release of the trigger, the drive collar rotates by an angular amount equivalent to the angular amount initially dialled in, and the plunger is advanced by the corresponding amount to deliver the dose of the required number of units.

This device performs extremely well and enjoys considerable success but we have identified a number of improvement opportunities. In the above device, in setting a dose the user winds up the spring to provide the motive force that is needed for the next dose. This means that it can be awkward for those of limited dexterity to exert sufficient grip to rotate the dose setting knob against the bias of the drive spring. Also in this design, because the action of dose setting winds up the drive spring, a ratchet action is required so that when the user releases their grip on the dose setting knob, the knob stays in that position and does not immediately return to the zero position under the influence of the drive spring. To allow dose setting reversal in case of setting overshoot, a bi-directional ratchet mechanism is then needed, or otherwise a disconnection mechanism is required, either of which complicate the device.

SUMMARY OF THE INVENTION

We have therefore designed an injector apparatus in which a clutch arrangement is provided to isolate the dose setting element from the force of the drive spring during the dose setting routine.

Accordingly, in one aspect, this invention provides an injector apparatus for use with a cartridge or syringe to deliver a plurality of doses therefrom, the injector apparatus comprising:
  a housing for the cartridge or syringe;
  a plunger for cooperating in use with the cartridge or syringe to express successive doses;
  a dose setting arrangement to select a dose volume;
  a drive mechanism releasable to advance said plunger in respective predetermined increments of magnitude to express said successive selected doses;
  characterised in that said drive mechanism includes a drive spring for applying expulsion drive movement directly or indirectly to said plunger, and said dose setting arrangement comprises a dose setting element moveable in a dose setting routine to set a magnitude of an increment of movement of said plunger for a given dose, said drive mechanism further including a clutch arrangement operable during said dose setting routine to isolate said dose setting element from the force of said drive spring and optionally to inhibit directly or indirectly forward movement of the plunger.

In an arrangement where the dose setting element is isolated from the force of the drive spring during the dose setting routine, the dose setting element can be rotated easily, and also preferably can be moved in the reverse sense if the user moves the dose setting element past a required dose. Isolating the dose setting element means that the dose-setting movement of said dose setting element is not resisted by said spring.

It follows from the above that if the dose setting action does not energise the drive spring, the drive spring needs to be energised in some fashion. Conveniently, the drive spring is preloaded to an extent sufficient to deliver substantially the entire useable contents of the syringe or cartridge in a succession of doses. Where the dose setting element is isolated from the force of the drive spring during the dose setting routine, a more powerful spring may be used than would be appropriate for the conventional user-wound device. Instead of providing a fully preloaded drive spring, the drive spring could be partially preloaded or with no preload but with suitable separate means for energising the spring. It will also be appreciated that in such arrangements the drive mechanism will usually already be under load from the drive spring prior to dose setting, in contrast to prior art devices where the drive mechanism is under load only once the dose has been dialled in.

Preferably, the dose setting element is moveable angularly to set said increment of plunger movement.

The clutch arrangement preferably includes a clutch element moveable between disengaged and engaged positions. Thus the clutch element may be adapted to move axially with said dose setting element, whereby axial movement of said dose setting element from a first, rest, position to a second, dose setting position causes said clutch element to engage to inhibit movement of said plunger. It is also convenient for the dose setting element and the housing to include complementary abutments that engage to prevent relative rotation of said dose setting element relative to said housing when the dose setting element is in its rest position, but which disengage to allow dose setting rotation of the dose setting element when it is in its setting position. In this manner, the dose setting element may be moved axially from its rest position to its dose setting position, then turned to dial in a required dosage volume, and then returned axially to its rest position to lock it against rotation.

Preferably, upon moving the dose setting element from its rest position to its setting position, the clutch engages to inhibit movement of the drive plunger a predetermined distance before the abutments on the dose setting element and the housing disengage to release the dose setting element for dose setting movement.

In a preferred arrangement, when the dose setting element is in its rest position, it receives and reacts the thrust of the drive spring so that the dose setting element thereby inhibits movement of the drive plunger. In this manner, when the dose setting element is in its rest position the thrust of the drive spring is reacted by the dose setting element and thence to the housing, but when the dose setting element is in its setting position, the thrust of the drive spring is reacted by the clutch member having engaged with the housing.

Preferably, having set a dose, returning the dose setting element axially to its first position disengages the clutch element to release the drive mechanism to cause the plunger to advance by a predetermined increment corresponding to the predetermined set dose.

Preferably, said plunger is threadedly engaged with an associated drive or control element whereby advance of said plunger is accompanied by rotation of the plunger or the drive or control element, with the magnitude of the incremental advance being set by constraining said rotation.

Preferably a stop member is associated with the dose setting element and is adjustable by moving the dose setting element, thereby to define an angular increment for the relative rotation between the plunger and the drive or control element upon release of the drive mechanism.

The stop member could simply be an abutment surface provided on the dose setting element. This would allow the maximum useable extent of angular movement of the dose setting element to be just short of 360°. This would mean that the indicia needed to be fairly closely packed in some instances. Accordingly it is preferred for there to be an intermediate dial or shuttle member threadedly engaged with the dose setting element and constrained to rotate with the rotatable one of the plunger and the control member, with the extent of relative angular movement of the dial or shuttle member and the dose setting element being set by the relative position of the stop member associated with the dose setting element. The provision of a threaded dial or shuttle member means that it is now possible to set a dose of several turns. This has advantages both in terms of the available size for the indicia, and also allows greater flexibility over the choice of the pitch of the thread between the plunger and the control member. In a particularly preferred arrangement, the dosage indicia may be provided as a helical strip on one of said complementary dose setting elements, and read off via a marker or window on the other dose setting element.

The drive spring in the various arrangements described above may be either a torsion spring that imparts a rotary movement when released, or a compression spring that imparts a linear movement.

In many applications it may be desirable to provide a multiple dose injector device that is supplied preloaded so that it is not necessary to re-energise the drive between each dose, for example if the device is intended to be disposable.

Accordingly, in another aspect, this invention provides an injector apparatus for use with a cartridge or syringe to deliver a plurality of doses therefrom, the injector apparatus comprising:

a housing for the cartridge or syringe;

a plunger for cooperating in use with the cartridge or syringe to express successive doses;

a dose setting arrangement to select a dose volume;

a drive mechanism releasable to advance said plunger in respective predetermined increments of magnitude to express said successive doses;

characterised in that said drive mechanism includes a rotary stored energy element with a preload sufficient to deliver at least a plurality of said successive doses.

In the above arrangement, the injector apparatus may for example be provided with a fully preloaded spring so that the user is not required to input the mechanical energy required to express the doses. This renders the device particularly suitable for those with limited dexterity or poor grip.

As noted above, conventional Autopen® and similar devices have an angular range of dose setting movement that is limited to 360°, and this places constraints on the marking indicia, the pitch of the drive thread, and the properties of the drive spring. We have therefore designed an arrangement in which the dose setting arrangement includes threadedly engaged first and second complementary dose setting elements which enables the dose setting movement to be several turns if required.

Accordingly, in another aspect of this invention, there is provided an injector apparatus for use with a cartridge or syringe to deliver a plurality of doses therefrom, the injector apparatus comprising:

a housing for the cartridge or syringe;

a plunger for cooperating in use with the cartridge or syringe to express successive doses;

a dose setting arrangement to select a dose volume;

a drive mechanism releasable to advance said plunger in respective predetermined increments of magnitude to express said successive doses and in which advance of said plunger is controlled by a control member that moves angularly in response to advance of said plunger;

characterised in that said dose setting arrangement includes first and second complementary dose setting elements threadedly engaged for relative threaded movement away from a limit position, with said first dose setting element being moveable relative to said housing in a setting routine from a rest position to a variable angular position that sets the dose volume, and said second dose setting element being constrained to rotate with said control member, whereby on release of said drive mechanism said control member and said second dose-setting element rotate until the second element returns to said first limit position with respect to the first element, thereby preventing further rotation of the control member.

According to another aspect, the invention provides an injector apparatus for use with a cartridge or syringe to deliver a plurality of doses therefrom, the injector apparatus comprising:

a housing for the cartridge or syringe;

a plunger for cooperating with the cartridge or syringe to express successive doses;

a drive mechanism energised by a drive spring, and releasable to advance said plunger in predetermined increments as determined by adjustment of a dose setting element, and a re-energising element for re-energising said spring independently of movement of said dose setting element.

Preferably said drive spring is a torsion spring and said re-energising element is a rotary element, for example a manually rotatable element.

According to another aspect, this invention provides an injection apparatus for use with a cartridge or syringe to deliver a plurality of doses therefrom, the injector apparatus comprising:

a housing for the cartridge or syringe;

a plunger for cooperating in use with the cartridge or syringe to express successive doses;

a dose setting element movable to select a dose volume;

a drive mechanism releasable to advance said plunger in respective predetermined increments of magnitude to express said selected dose volumes, said drive mechanism including a drive spring for providing motive force directly or indirectly to said plunger to advance said plunger, and the apparatus being configurable between a first position in which the motive force of the drive spring is transmitted via the dose setting element to the housing to be reacted thereby, and a second position in which a clutch element is moved into a position in which motive force of the drive spring is transmitted via the clutch element to the housing to be reacted thereby, so that dose setting movement of the dose setting element is not resisted by the drive spring.

Whilst the invention has been described above, it extends to any inventive combination of the features set out above or in the following description of claims.

BRIEF DESCRIPTION OF THE DRAWINGS

The invention may be performed in various ways, and an embodiment thereof will now be described by way of example only, reference being made to the accompanying drawings in which:

FIG. 1 is a side view of a first embodiment of pen injector in accordance with this invention:

FIG. 2 is a side section view of the pen injector of FIG. 1;

FIG. 4 is an enlarged view of the main body of the pen injector of FIGS. 1 to 3, containing the drive mechanism, with one body half shown transparent;

FIG. 5 is a perspective section view of the dose setting knob showing the thread on the inside of the dose setting knob;

BRIEF DESCRIPTION OF THE PREFERRED EMBODIMENTS

Figure 3:
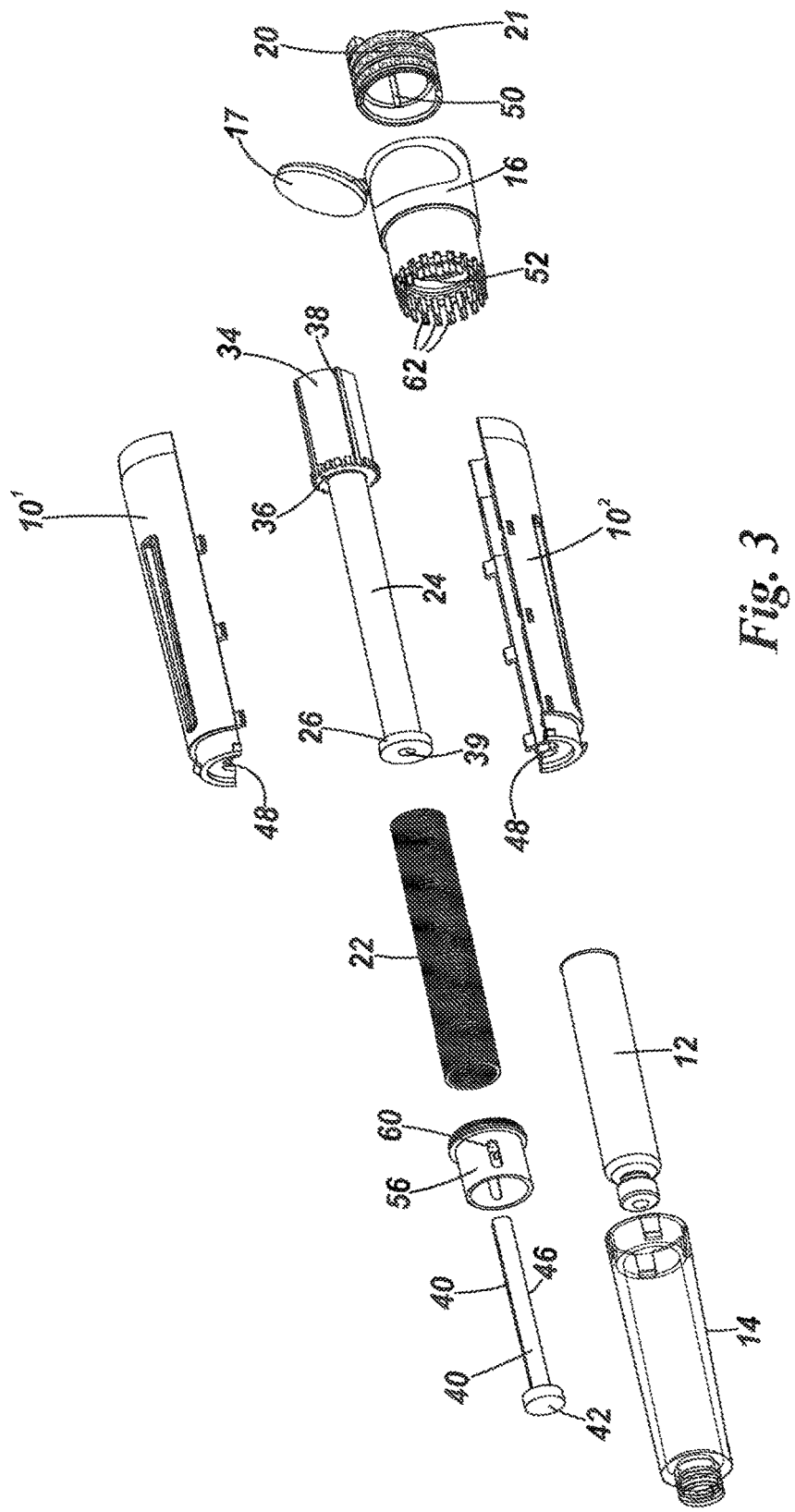
FIG. 3 is an exploded view of the pen injector of FIGS. 1 and 2.

The embodiment of pen injector illustrated in FIGS. 1 to 6 is designed to be a disposable automatic pen type injector capable of expelling a succession of doses of variable preset magnitude from a cartridge. The injector comprises a body made up of symmetric body halves $10^1$ and $10^2$ which may be snap-fitted or glued together. A cartridge or syringe 12 is received in a transparent forward cartridge housing 14 which is a snap-fit on the forward end of the body halves $10^1$, $10^2$. On the rear end of the body is mounted a dose setting knob 16 having a window 18 through which a dose dial 20 is visible. As to be described below, the device contains a preloaded torsion spring which in this particular embodiment supplies the entire force required to express all the useable dosage volume in the cartridge. Doses are set by pulling the dose setting knob 16 rearwardly, rotating it until the required dosage unit is visible on the dose dial and then pushing the dose dial back in to release the drive mechanism to expel the required dose.

Referring now more particularly to FIGS. 2, 3 and 4 the body $10^1$, $10^2$ defines an internal cylindrical space in which a torsion spring 22 is located in an energised state, with the forward end of the spring being anchored on an inner part 23 of the body. A hollow tubular drive shaft 24 is disposed concentrically within the spring having a radial flange 26 which is rotatably held within an annular recess 28 on the forward part of the body to allow rotation of the drive shaft but to prevent axial movement thereof. Towards its rear end, the diameter of the shaft increases at a shoulder 30 in which is provided an anchorage hole 32 for the rear end of the drive spring. When assembled and prior to first use, the torsion spring 22 is fully energised and acts on the drive shaft to rotate it in the dispensing direction. The enlarged portion 34 at the rear end of the drive shaft is provided with upstanding splines 36 adjacent the shoulder 30, with four of the splines 38 at $90^2$ extending the full length of the enlarged portion 34.

At the front end the drive shaft has an internally threaded bore 39 into which is threaded the lead screw of a plunger 40. The plunger has an enlarged head 42 which engages the bung 44 of the cartridge 12. Immediately behind the enlarged head 42 the drive shaft has two diametrically opposed keyways 46 which cooperate with respective keys 48 on the front end of the body halves $10^1$ and $10^2$, to allow axial movement of the plunger, but prevent rotation thereof, as the drive shaft 24 rotates to advance the plunger.

The dose dial 20 is slideably mounted on the enlarged portion 34 of the drive shaft 24 but prevented from rotation thereof by means of four, internal, equispaced, keyways 50 that engage the longer splines 38 on the enlarged portion. The forward end of the dose dial has an enlarged internal diameter so as to be clear of the shorter splines 36. The external surface of the dose dial 20 carries a coarse helical thread 21 which threadedly engages a corresponding internal threaded portion 52 on the inner surface of the dose setting knob 16. The threaded portion 52 on the inside of the dose setting knob 16 has a forward limit position set by termination of the thread (see blind end 54 in FIG. 5). A rear limit position stop may optionally be provided, for example, on the inner part of a hinged cap portion 17 of the dose setting knob.

Figure 6:
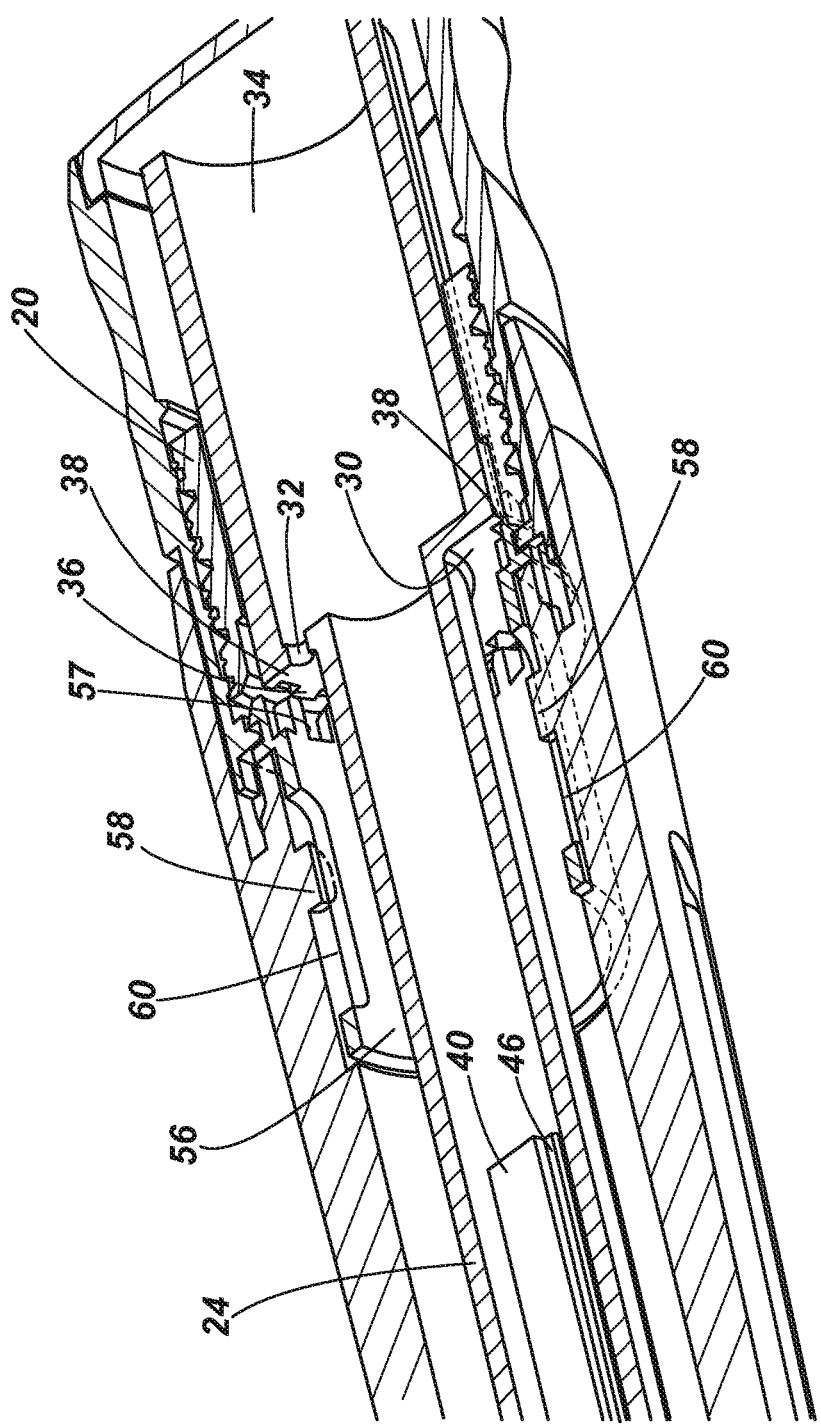
FIG. 6 is a perspective section view on the rear part of the drive mechanism showing the clutch and dose setting knob and dose dial.

The dose setting knob 16 is connected at its forward end to a clutch collar 56 by means of a snap-fit which allows the clutch and the dose setting knob to rotate relative to each other but secures them against relative axial movement (see FIG. 6). The clutch collar 56 is mounted for axial sliding movement in the body 10 but prevented from rotation with respect thereto by means of two lugs 58 in the body engaging opposed respective slots 60 in the cylindrical wall of the clutch collar 56. At its rear end, the clutch collar 56 has an internal splined arrangement 57 designed to slide into splined engagement with the splines 36 on the enlarged portion 34 of the drive shaft so as to lock the drive shaft against movement under the influence of the spring by reacting the thrust into the body by via the lugs 58. Referring now more particularly to FIGS. 4 to 6, the forward end of the dose setting knob 16 has a series of axially extending fingers 62 which are an axial sliding fit with a series of pockets 64 provided in the body.

The axial lengths of the fingers 62 and of the pockets 64 are carefully selected having regard to the axial spacing between the internal splines 57 on the clutch collar 56 and the external splines 36 on the drive shaft 24 such that, on pulling the dose setting knob 16 out axially, the splines 57 on the clutch collar 56 engage the splines 36 on the drive shaft 24 some distance before the fingers 62 of the dose setting knob 16 are withdrawn axially from the pockets 64 on the body. The reason for this is that, in the position shown in FIG. 2, as indicated above, the thrust of the drive spring is transmitted via the drive shaft splines 38 to the dose dial 20 and thence to the dose setting knob 16 (by virtue of the dose dial being at its forward limit position relative to the dose setting knob). It is therefore important to ensure that the clutch 56 has engaged the drive shaft 24 to react the load of the torsion spring 22 through the clutch 56 and the lugs 58 to the housing before the dose setting knob has withdrawn enough to rotate.

Once the dose setting knob has been withdrawn far enough to disengage the fingers 62 from the pockets 64, it is in a setting position in which it may be rotated to set a dose against a light detent action provided by the fingers 62, which provide a audible/tactile click to enable the user to count the number of units dialled in. It will be appreciated that during dose setting, the body 10, drive shaft 24, clutch 56 all remain stationary, both axially and rotationally. The dose dial is fixed against rotation due to its splined engagement with the large portion 34 of the drive shaft but is capable of moving axially. Thus in this condition, with the dose setting knob 16 axially in its setting position, rotation of the dose setting knob in the appropriate direction moves the dose dial 20 axially in a lead screw fashion. The dose dial numbers are visible through the window 18. The threaded arrangement allows multiple turns of the dose setting knob. Also at this point there is no loading between the dose dial and the cap and so there is little resistance to rotary movement of the dose setting knob apart form that provided by the detent.

Once the required dose has been dialled in on the helical scale, the device is ready for firing. In this arrangement this is achieved by pushing the dose setting knob 16 back in. As the dose setting knob is pushed back in, the fingers 62 re-engage the pockets and thereafter the clutch 56 is shifted forwardly off the enlarged portion of the drive shaft to disengage it so that the drive shaft is now free to rotate. The drive shaft rotates by the angular amount dialled in.

In the above arrangement, as the setting of the dose is independent of the drive spring, the operating stroke length and force can be reduced to design a device in which a large dose is delivered with a small movement and force. This contrasts with existing devices in which the user has to apply a large user movement to set a dose and/or expel the set dose.

There is a potential issue in existing multi-dose devices in which after expulsion of a dose the plunger remains in contact with the bung. Due to the friction between the bung and the cartridge wall and its resilience, at the end of an injection the bung will be under residual compression. Vibrations transmitted to the bung either via the plunger or the wall of the cartridge can cause the bung to expand slightly and expel a drip which can affect dose accuracy. As a modification of the above embodiment the clutch arrangement can be designed so that, as it is pulled to disengage, it backs off the plunger 40 from the bung 44 a fraction, so that the bung 44 is unloaded.

This unloading effect may be achieved for example by putting a slight form on the splines 57 of the clutch collar 56 and on the splines 36 of the drive shaft 24 so that, as the dose setting knob is pulled out to engage the clutch collar 56 on the drive shaft, the drive shaft is rotated a few degrees against the spring bias to unload the bung.

Whilst in this embodiment the body is formed in two separate halves it may instead be formed in a clamshell type arrangement where the two halves are hinged by a live hinge.

In order to ease manufacture, the torsion spring in the illustrated embodiment may be formed with a wave or compression portion at its forward end to apply a light axial load to the cartridge in order to hold the cartridge firmly in a forward position. This allows variations in length due to production variances to be accommodated. Furthermore although the wire that is coiled to make the spring may be circular in section in some applications it is preferred for it to be non-circular, such as of square or rectangular section.

Figure 7:
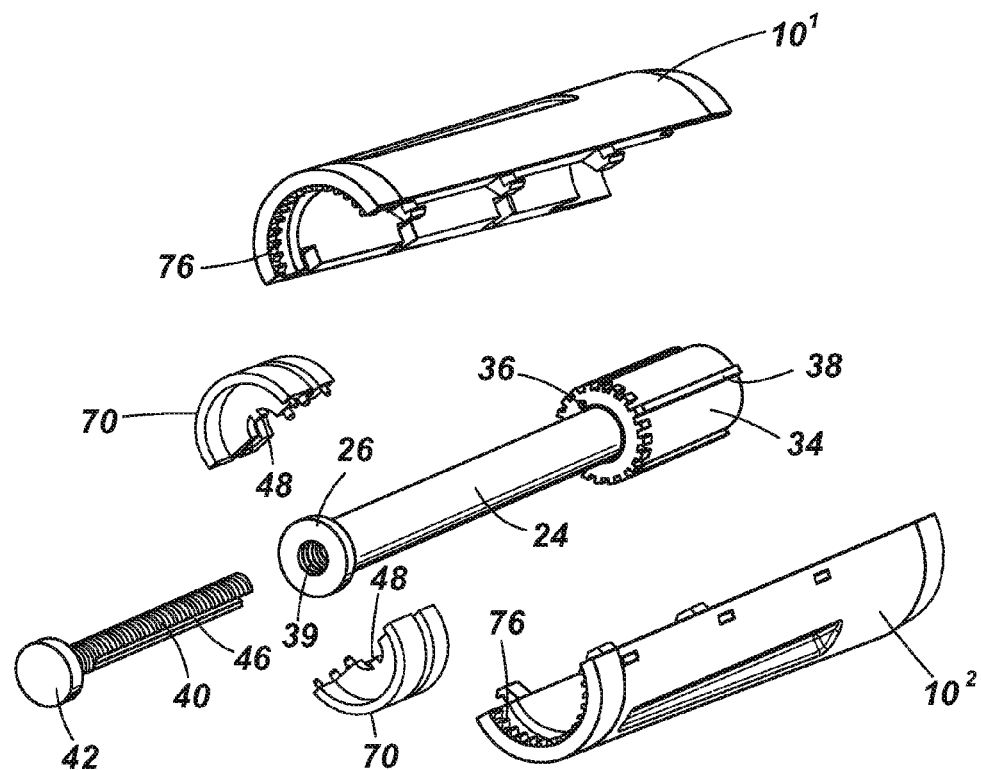
FIG. 7 is an exploded view of a second embodiment of pen injector in accordance with the invention having a rewind facility.
Figure 8:
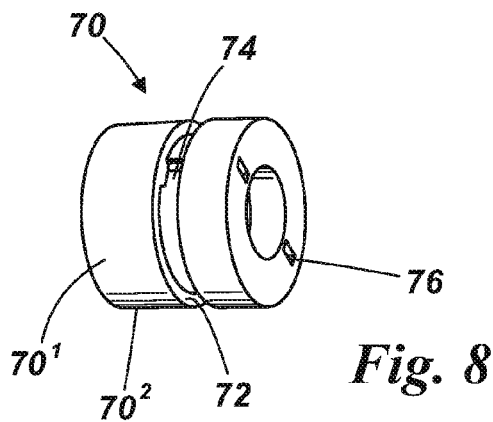
FIG. 8 is a detailed view of the rewind knob.

Referring now to FIGS. 7 and 8, a second embodiment provides an arrangement for rewinding the plunger 40 and simultaneously energising the drive spring 22 (see FIGS. 3 and 4) of the first embodiment. In the second embodiment most of the components are similar to those of the first embodiment and will not be described again and will be given like reference numerals. Referring to FIG. 7, the forward part of the housing which defines the keys 48 that engage the keyways 46 on the lead screw of the plunger is formed as a separate rewind knob 70 which is uni-directionally rotatable about the longitudinal axis of the housing. The knob 70 is formed in two halves $70^1$, $70^2$ and defines a central aperture with the diametrically opposed keys 48. The knob 70 has an outer circumferential groove 72 in the base of which are two diametrically opposed sprung ratchet teeth 74, as seen in FIG. 8. The knob 70 is rotatably received in the forward end of the housing by means of an inwardly directed toothed annular rib 76 locating in the groove 72 and cooperating with the ratchet teeth 74 to allow rotation in one direction only. The rear end of the rewind knob 70 is provided with two slots 76 into one of which the front end of the torsion drive spring 22 (not shown) is anchored. Engagement of the keys 48 on the knob 70 with the keyways 46 on the lead screw of plunger 40 ensures that the plunger 40 rotates with the knob in one direction only but is capable of axial sliding movement. The knob and the plunger may therefore be rotated in the direction permitted by the ratchet to wind up the drive spring 22 and to retract the plunger back into the driveshaft 24 by virtue of the threaded engagement between the lead screw of the plunger 40 and the driveshaft.

The rewind knob will normally be accessible only when the cartridge housing (see first embodiment) has been removed from the body.

Figure 9:
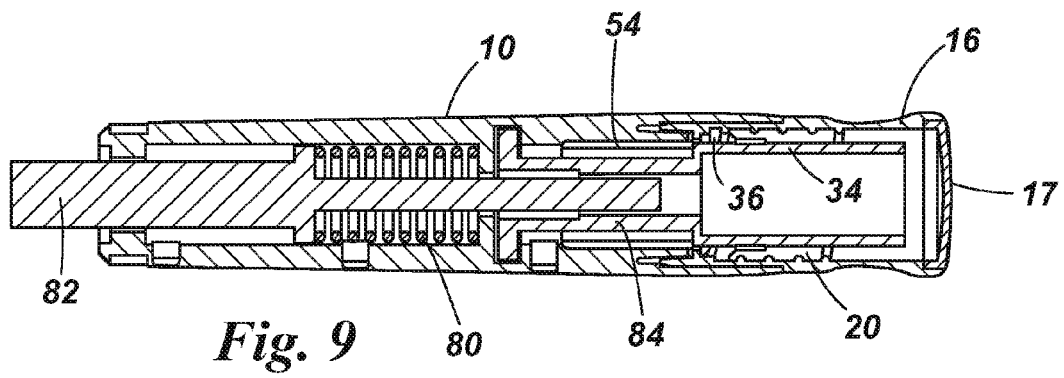
FIG. 9 is a side section view of a third embodiment of pen injector driven by a compression spring.

In the above arrangements, a torsion spring provides the motive force for expelling the useable contents of the cartridge. It would of course be possible to use other suitable drive configurations. For example, as shown in FIG. 9, the torsion spring could be replaced by a compression spring 80 which acts on the plunger 82 to apply a thrust in the longitudinal direction. In this case, instead of the drive shaft there is a drive control shaft 84 that is used to modulate forward movement of the plunger 82 under the influence of the compression spring 80.

The rear end of the plunger 82 is formed with a threaded portion which threadedly engages an internal bore on the drive control shaft 84 so that as the plunger 82 is urged forwardly by the compression spring the drive control shaft rotates. The drive control shaft 84 is formed at its rear end with an enlarged portion 34 provided with upstanding splines 36 similar to those of the drive shaft 24 of the first embodiment, and fulfilling a similar function in conjunction with a clutch collar 56, the dose setting knob 16 and the dose dial 20 of the first embodiment. The construction and operation of these elements will not be described in detail again. As previously, the drive control shaft 84 is alternately held and released by the clutch collar 56 and the dose setting knob 16.

The invention claimed is:

1. An injector apparatus for use with a cartridge or syringe to deliver to a user a plurality of doses from an initial volume, the injector apparatus comprising:
   a housing for the cartridge or syringe;
   a plunger that, in use, advances relative to the cartridge or syringe from an initial position to plural successive positions to express successive doses, including an initial dose from said initial volume, and at least one further dose from a remainder of said initial volume;

a dose setting arrangement that includes a dose setting element operable by the user to select a dose volume in a dose setting routine, the dose volume defining a magnitude of an increment of movement of said plunger for a given dose; and a drive mechanism, including an energized rotary stored energy element releasable to advance said plunger in respective predetermined increments of magnitude to express said successive doses, said energized rotary stored energy element having been energized without user input prior to a first use of the injector apparatus by the user with a preload sufficient to deliver said successive doses, said drive mechanism being under load from the energized rotary stored energy element prior to user operation of the dose setting arrangement, and, in operation, a release of said energized rotary stored energy element of said drive mechanism causes said plunger to be driven from said initial position to a first of said plural successive positions, and a subsequent release of said energized rotary stored energy element causes said plunger to be driven from at least the first of said plural successive positions to at least a second of said plural successive positions, wherein said drive mechanism further includes a clutch arrangement operable during said dose setting routine to inhibit forward movement of the plunger.

2. The injector apparatus according to claim 1, wherein, before any use by the user, said energized rotary stored energy element is preloaded, prior to the user's selecting a dose volume, and without the user inputting a mechanical energy required to express the selected dose volume, to a magnitude sufficient to deliver an entire usable contents of the syringe or cartridge over a succession of doses.

3. The injector apparatus according to claim 2, further comprising:
means for re-energising said energized rotary stored energy element.

4. The injection apparatus according to claim 1, wherein said energized rotary stored energy element comprises a torsion spring.

5. The injector apparatus according to claim 1, wherein said dose setting element is moveable angularly to define said increment of plunger movement.

6. The injector apparatus according to claim 5, wherein said clutch arrangement includes a clutch element moveable between a disengaged position and an engaged position.

7. The injector apparatus according to claim 6, wherein said clutch element is adapted to move axially with said dose setting element, whereby axial movement of said dose setting element from a first rest position to a second dose-setting position causes said clutch element to engage to inhibit forward movement of the plunger.

8. The injector apparatus according to claim 7, wherein said dose-setting element and said housing include complementary abutments that engage to prevent relative rotation of said dose setting element relative to said housing when said dose setting element is in the first rest position, but disengage to allow relative rotation therebetween when said dose setting element is in the second dose-setting position.

9. The injector apparatus according to claim 8, wherein upon moving said dose setting element from said first rest position to said second dose-setting position, said clutch element engages before engagement of the abutments on said dose setting element and said housing.

10. The injector apparatus according to claim 7, wherein a thrust of the energized rotary stored energy element is reacted by said dose setting element when said dose setting element is in the first rest position.

11. The injector apparatus according to claim 7, wherein returning said dose setting element to said first resting position after having set a predetermined dose disengages the clutch element to release the drive mechanism to cause said plunger to advance by a predetermined increment corresponding to said predetermined set dose.

12. The injector apparatus according to claim 1, wherein said plunger is threadedly engaged with an associated control element, whereby linear movement of said plunger is accompanied by rotation of one of the plunger and the associated control element, and the magnitude of the increment of movement is controlled by limiting said rotation.

13. The injector apparatus according to claim 12, wherein a stop surface associated with said dose setting element, is adjustable on movement of said dose setting element to define an angular increment of movement for the relative rotation between the plunger and the associated control element upon release of said drive mechanism.

14. The injector apparatus according to claim 13, wherein an intermediate shuttle member is threadedly engaged with said dose setting element and is constrained to rotate with the rotatable one of the plunger and the associated control element, with an extent of relative angular movement of the shuttle member and the dose setting element being set by a relative position of the stop surface associated with the dose setting element.

15. An injector apparatus for use with a cartridge or syringe to deliver to a user a plurality of doses from an initial volume, the injector apparatus comprising:
a housing for the cartridge or syringe;
a plunger that, in use, advances relative to the cartridge or syringe from an initial position to plural successive positions to express successive doses, including an initial dose from said initial volume, and at least one further dose from a remainder of said initial volume;
a dose setting arrangement operable by the user to select a dose volume; and
a drive mechanism releasable to advance said plunger in respective predetermined increments of magnitude to express said successive doses,
wherein said drive mechanism includes an energized rotary stored energy element, said energized rotary stored energy element having been energize without user input prior to a first use of the injector apparatus by the user with a preload sufficient to deliver said successive doses,
said drive mechanism being under load of the preload of the energized rotary stored energy element prior to user operation of the dose setting arrangement and, in operation, and release of the energized rotary stored energy element of said drive mechanism driving said plunger from said initial position to a first of said plural successive positions, and subsequently from the first of said plural successive positions to at least a second of said plural successive positions, and
wherein said dose setting arrangement comprises a dose setting element moveable in a dose setting routine to define a magnitude of an increment of movement of said plunger for a given dose, said drive mechanism further including a clutch arrangement operable during said dose setting routine to inhibit forward movement of the plunger.

* * * * *